United States Patent [19]

Schaldach

[11] Patent Number: 5,336,243

[45] Date of Patent: Aug. 9, 1994

[54] PHYSIOLOGICALLY CONTROLLED PACEMAKER AND PACEMAKER CONTROL SYSTEM WITH DETECTION OF THE SPATIAL POSITION OF THE PATIENT

[75] Inventor: Max Schaldach, Erlangen, Fed. Rep. of Germany

[73] Assignee: Biotronik Mess- und Therapiegerate GmbH & Co., Ingenieurburo Berlin, Berlin, Fed. Rep. of Germany

[21] Appl. No.: 31,911

[22] Filed: Mar. 16, 1993

Related U.S. Application Data

[63] Continuation of Ser. No. 859,446, May 29, 1992, abandoned.

[30] Foreign Application Priority Data

Nov. 29, 1989 [DE] Fed. Rep. of Germany ....... 3939900

[51] Int. Cl.[5] ............................................. A61N 1/365
[52] U.S. Cl. ........................................ 607/18; 128/782
[58] Field of Search ............................ 607/18; 128/782

[56] References Cited

U.S. PATENT DOCUMENTS

| | | | |
|---|---|---|---|
| 4,771,780 | 9/1988 | Sholder | 128/419 pG |
| 4,773,401 | 9/1988 | Citak et al. | 128/419 PG |
| 4,846,194 | 7/1989 | Alt | 128/782 |
| 4,865,036 | 9/1989 | Chirife | |
| 4,873,980 | 10/1989 | Schaldach | 128/419 PG |
| 4,877,032 | 10/1989 | Heinze et al. | 128/419 PG |
| 4,919,137 | 4/1990 | Schaldach | 128/419 PG |
| 5,040,536 | 8/1991 | Riff | 128/419 PG |

FOREIGN PATENT DOCUMENTS 0225839 6/1987 European Pat. Off. .
0259658 3/1988 European Pat. Off. .

OTHER PUBLICATIONS

M. Schaldach: "Present State and Future . . . ", 680 Medical Progress through Technology, 13 (1987), No. 2, Dordrecht, NL.
M. Schaldach: "PEP-gesteuerter Herzschrittmacher", Biomedizinische Technik, 34, Jul.-Aug. 1989.
Biomed. Technik 34 (1989), 191–196, "Motion Energy As A control Variable for Sensor-Driven Rate Adaptation," M. Hubmann et al.

Primary Examiner—William E. Kamm
Attorney, Agent, or Firm—Spencer, Frank & Schneider

[57] ABSTRACT

A cardiac pacemaker control system includes a stress detector system (1) for producing a controlled basic stimulation rate based on signals picked up within a patient's body related to physical stress and derived from a pre-ejection period of the patient. A detection device (10, 15) detects a spatial orientation of the patient, and produces an output switching signal (20) for changing the controlled basic stimulation rate depending upon the position of the patient which represents an additional measure of physical stress.

9 Claims, 2 Drawing Sheets

PHYSIOLOGICALLY CONTROLLED PACEMAKER AND PACEMAKER CONTROL SYSTEM WITH DETECTION OF THE SPATIAL POSITION OF THE PATIENT

This application is a continuation of application Ser. No. 07/859,446, filed May 29, 1992 now abandoned.

BACKGROUND OF THE INVENTION

The invention relates to a cardiac pacemaker according to the preamble of claim 1.

The publication "Biomed. Technik [Biomedical Technology], 34 (1989), pages 177–184"0 discloses a PEP [pre-ejection period] controlled cardiac pacemaker. The term PEP is understood to mean the interval from the beginning of chamber depolarization to the beginning of the ejection phase. The implantable stimulation system presented there, which includes PEP controlled physiological frequency regulation, is based on the relationship between the PEP and the chronotropic heart rate. The shortening of the PEP can be converted to an increase in frequency. In the case of a decrease of the adrenergic effect, both intervals are extended. The solution disclosed there is based on the right ventricular intracardial detection of a time interval from the impedance curve obtained between the electrode tip and the pacemaker housing which coincides well with the left ventricular PEP.

The "ideal" physiological parameter for a controlled adaptation of the stimulation rate of an artificial cardiac pacemaker reflects physical or emotional stress but is independent of the cardiac frequency. The frequency can be determined with the aid of a truth table or as a functional relationship from the momentarily measured value of the physiological parameter. The tensioning time, the PEP, has these "ideal" characteristics. In a constant stress situation, the PEP is independent of the stimulation rate and with a constant stimulation rate, it is an unequivocal function of stress.

If, however, the PEP is employed as a physiological parameter for the controlled adaptation of the stimulation rate of an artificial cardiac pacemaker, the purely static stress on the basis of the volume of blood involved must be considered. This static stress differs because of the distribution of the blood in the artery system in the standing or recumbent state. Although the above-mentioned literature citation depicts, at page 183, FIG. 13, an algorithm which, in the longer duration rest case, is based on a patient in a recumbent position, this algorithm is inaccurate and not suitable to ensure quick adaptation of the heart rate to actual stress conditions.

SUMMARY OF THE INVENTION

It is the object of the invention to provide a cardiac pacemaker and control system which considers the actual stress during PEP control.

This is accomplished in a cardiac pacemaker as defined in the preamble of claim 1 by the features defined in its characterizing portion.

Modifications and advantageous features of the invention are defined in the claims, the description below and the drawings.

According to the invention, the actual stress is considered in a PEP controlled cardiac pacemaker in the form of different stress/stimulation rate relationships. This can be effected to advantage in a processor controlled cardiac pacemaker by switching between tables that are stored in a memory. A position sensor is employed according to the invention as the detection device for the patient's position and to generate a switching signal. This sensor may be, for example, a gravity controlled switch.

As a further solution, it is proposed to adapt the relationship between stress and stimulation rate, which is essentially proportional, to the actual stress by changing a factor.

With the switching, according to the invention, between the different stress/stimulation rate relationships depending on the patient's momentary position (recumbent or standing) with normal operation of the heart and circulatory system, the heart rate is advantageously set lower for the recumbent state to correspond to physiological requirements. Without switching, the heart rate would rise due to the absence of the static bias.

BRIEF DESCRIPTION OF THE DRAWINGS

The invention will now be described in greater detail with reference to the drawing, in which.

DETAILED DESCRIPTION OF THE PREFERRED EMBODIMENTS

Figure 1:
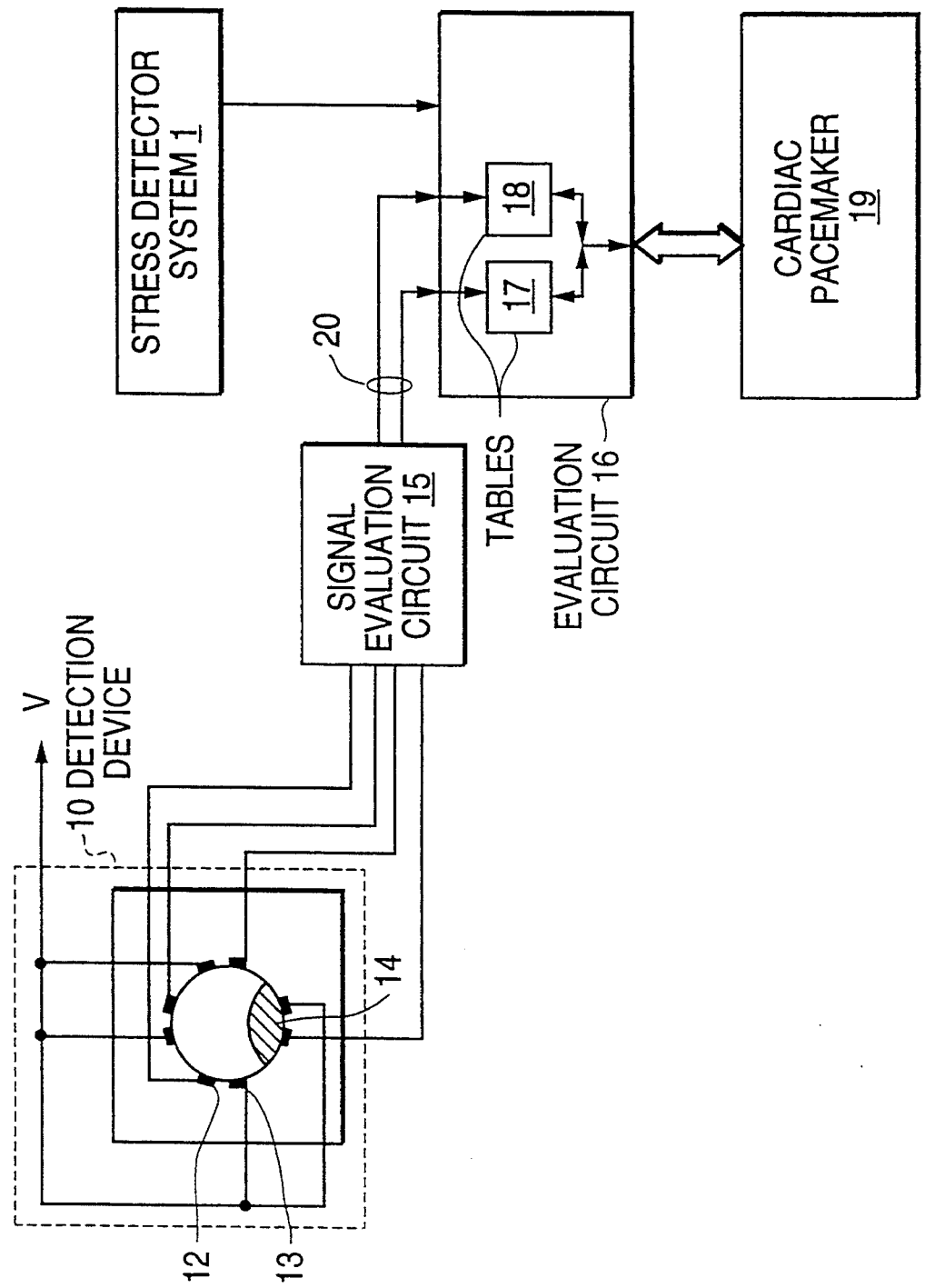
FIG. 1 depicts a first embodiment of a cardiac pacemaker exhibiting the measures according to the invention.

The first embodiment of a cardiac pacemaker 19 according to the invention as shown in FIG. 1 includes an evaluation circuit 16 for use of the PEP from stress detector system 1, as the physiological parameter for the controlled adaptation of the stimulation rate. Evaluation circuit 16 receives a signal from a signal evaluation circuit 15 in a detection device 10 for switching between tables 17 and 18. Detection device 10 may be, for example, a gravity controlled switch. In the drawing, a mercury switch 11 including switch contacts 12 and 13 and a mercury bead 14 are shown as an example. One contact 13 of the pair of contacts 12 and 13 is connected with the supply voltage V, the other contact 12 leads to an input of signal evaluation circuit 15. Depending on the patient's position, signal evaluation circuit 15 detects whether the patient is in a horizontal or vertical position. Depending on the detected position, signal evaluation circuit 15 generates a switching signal 20 to adapt the stress/stimulation rate relationships to the patient's position.

In the illustrated example this is accomplished by the use of the appropriate table 17 or 18 for the evaluation of the stress/stimulation rate relationships.

Figure 2:
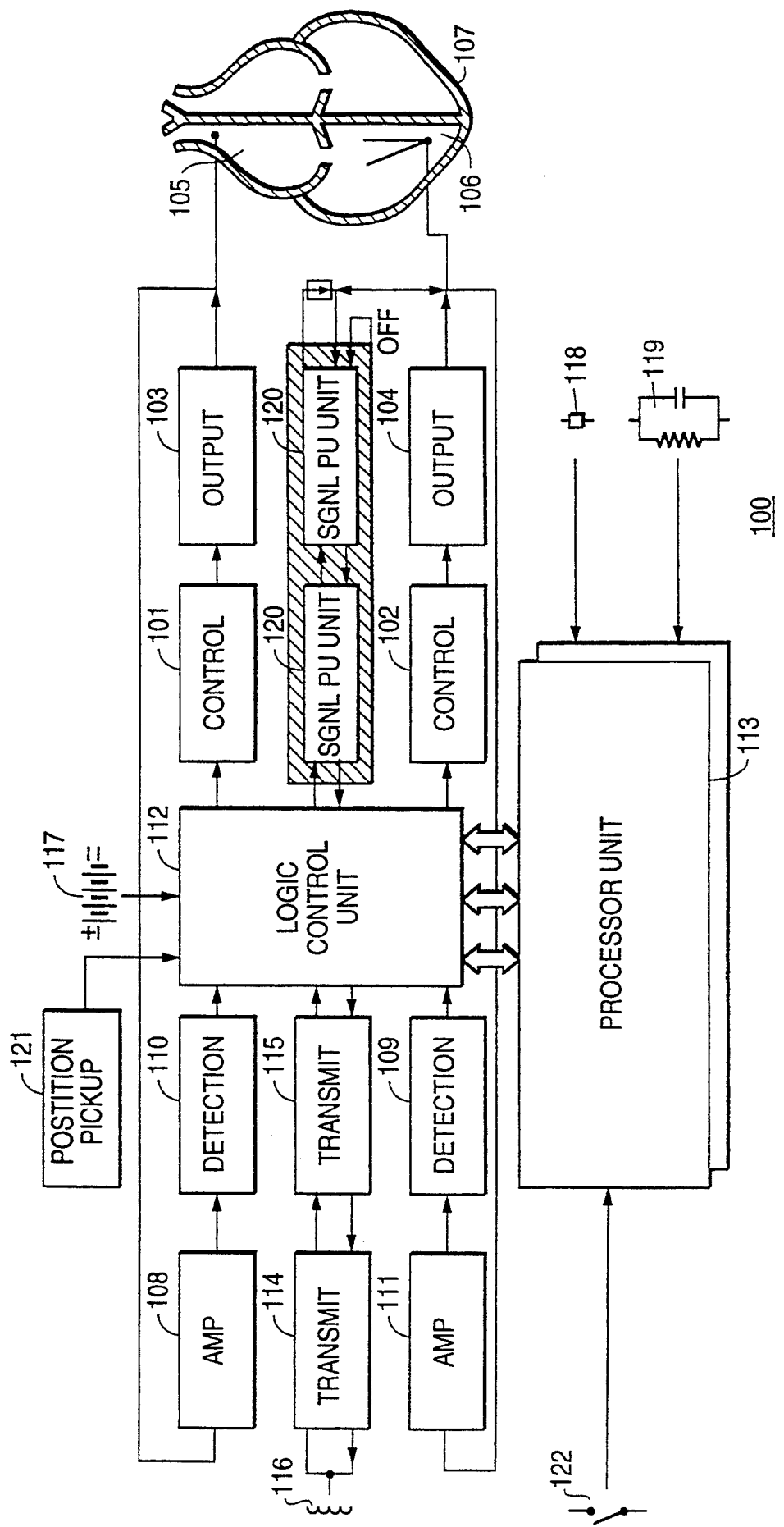
FIG. 2 is a complete block circuit diagram for a rate controlled cardiac pacemaker.

FIG. 2 is a block circuit diagram for a rate controlled cardiac pacemaker 100. This cardiac pacemaker stimulates by way of control stages 101 and 102, respectively, and output stages 103 and 104, respectively, the atrium 105 and ventricle 106, respectively, of the heart 107 by means of appropriate electrodes that are connected to the output circuits. These electrodes also receive signals that are characteristic for actions from the heart proper and feed these signals to an input amplifier circuit 108 and 111, respectively. These signals are processed by way of subsequently connected detection stages 110 and 109, respectively - in each case separately for atrium and ventricle.

These data are conducted to a processor system 113 by way of logic control unit 112. This processor system 113 is connected with the logic control unit 112 by way of a data bus, a control bus and an additional bus so that the digitized signals picked up in the atrium and ventricle can be read out from the processor unit 113 and additionally digital control signals can be output to generate stimulation pulses in the atrium and ventricle. Logic control unit 112 has the same relationship to processor unit 113 as a control unit for a peripheral unit, for example, as an interface equipped with an A/D-D/A converter for picking up and putting out external analog signals, often also called an input-output unit.

Also connected with the logic control unit 112 is a bidirectional transmission channel 114, 115 which is able to transmit by means of an inductance 116 signals picked up from the heart to outside of the patient and also control signals for programming the cardiac pacemaker from outside of the patient to the pacemaker. Further provided is a battery 117 for supplying the entire pacemaker, a quartz crystal 118 and a resonant circuit 119 as timer or reserve timer, respectively.

A signal pickup unit 120 serves to determine a physiological parameter within the patient's body which constitutes a measure for physical stress. In the illustrated embodiment, this unit is a pulse generator for putting out measurement pulses (current pulses i) in the right ventricle from which can be determined, by way of the electrode disposed in the ventricle, the momentary electrical resistance within the ventricle at predetermined times. Circuit 120 further includes a line for disconnecting this module so that the emission of current pulses, in particular, is prevented. Block 120 can be disconnected from logic control unit 112 by means of an "off" signal. This disconnection is effected by processor unit 113.

Finally, a position pickup 121 is provided which detects changes in the physical situation of the patient and particularly changes in position, that is, a change from a recumbent to a standing position. The position pickup is connected with processor system 112 for direct data exchange. By means of a reed switch 122 and an external magnet, processor unit 113 can be put into a predetermined state in which stimulation is preferably effected at a fixed rate.

In the embodiment illustrated here, the memory addressed within processor unit 113 is changed as a result of a signal output by the position sensor so that the informations corresponding to the respective body position are read out from the addressable memories of this unit. If the body positions are different but otherwise the signals representing the physical stress are identical, control values for the basic stimulation rate are put out which compensate the different measured values for identical physical stress but different body positions.

In another preferred embodiment of the invention, repeated output signals from position pickup 121 indicating a change in the patient's position are utilized as a (further) measure for the input value representing the physical activity of the patient. The evaluation here corresponds to that for the PEP value which here constitutes a measure for physical stress.

The invention is not limited in its embodiments to the above-described preferred embodiment. Rather, a number of variations are conceivable which take advantage of the described solution even for basically different configurations. For example, instead of employing appropriate tables, corresponding functions may also be employed. It is also possible to perform an evaluation by means of discrete components.

What is claimed is:

1. A cardiac pacemaker control system for controlling a stimulation pulses of a cardiac pacemaker, including:
   stress detector means for controlling a basic stimulation rate of the cardiac pacemaker, by picking up signals within a patient's body related to physical stress and producing signals for physical stresses derived from a pre-ejection period of the patient; and
   a orientation detection means including a position pickup, for detecting a spatial orientation of the patient, and outputting a switching signal for changing the basic stimulation rate depending upon the position of the patient which represents an additional measure of physical stress.

2. A cardiac pacemaker according to claim 1, wherein said orientation detection means comprises an evaluation circuit having a plurality of memory tables including memory locations, wherein the switching signal switches between the memory tables, wherein the memory locations of the memory tables contain prestored information representing respective associations between physical stress and the basic stimulation rate, wherein different information contained in respective memory locations of the respective memory tables is thereby addressed by the stress detector means and the switching signal as a result of the signals for physical stresses derived from a pre-ejection period of the patient and the switching signal representing the spatial orientation of the patient, and wherein the respective information prestored in the respective memory locations of the respective memory tables differs by a correction value related to a difference in spatial orientation of the patient.

3. A cardiac pacemaker according to claim 2, wherein the evaluation circuit comprises a control unit having a microprocessor, wherein the memory tables are a component of the control unit.

4. A cardiac pacemaker according to claim 1, wherein the orientation detection means comprises a gravity controlled switch.

5. A cardiac pacemaker according to claim 1, wherein the changing of the basic stimulation rate initiated by the switching signal is changed by multiplication means based on a constant factor.

6. A cardiac pacemaker according to claim 1, wherein repeated output signals from the position pickup of the orientation detection means within a predetermined time interval indicates physical stress and causes the orientation detection means to output the switching signal.

7. A system for switching between different stress/stimulation rate relationships for controlling a cardiac pacemaker, said system comprising:
   stress detection means for detecting a pre-ejection period of a patient and producing pre-ejection period control signals;
   detection means for detecting a spatial orientation of a patient and producing position signals;
   position signal evaluation means for receiving the position signals from the detection means, determining whether the patient is in a horizontal or a vertical orientation, and producing a switching signal based on the determining;
   evaluation means, including a first memory table and a second memory table, said evaluation means for receiving the pre-ejection period control signals from the stress detection means and the switching signal from the position signal evaluation means, for switching between the first and second memory tables in accordance with the received signals, and for providing output from the memory tables to control a cardiac pacemaker in accordance with respective stress/stimulation rate relationship data in said memory tables.

8. The system for switching between different stress/stimulation rate relationships for controlling a cardiac pacemaker according to claim 7, wherein said detection means for detecting a spatial orientation of a patient and producing position signals comprises a gravity controlled switch.

9. The system for switching between different stress/stimulation rate relationships for controlling a cardiac pacemaker according to claim 8, wherein said gravity controlled switch comprises a memory switch including a plurality of switch contacts disposed thereon and a mercury bead which closes different ones of said contacts depending on the position of the mercury switch, whereby the orientation of the patient, which is indicative of physical stress, is indicated by the position of the mercury switch which is indicated by which of said contacts are closed.

* * * * *